United States Patent
Ozaita Mintegui et al.

(10) Patent No.: US 9,662,320 B2
(45) Date of Patent: May 30, 2017

(54) ANTAGONISTS OF THE CANNABINOID RECEPTOR CB1 FOR USE IN THE TREATMENT OF DISEASES ASSOCIATED WITH NEURONAL DENDRITIC ABNORMALITIES

(71) Applicant: Universitat Pompeu Fabra, Barcelona (ES)

(72) Inventors: Andres Ozaita Mintegui, Barcelona (ES); Arnau Busquets Garcia, Barcelona (ES); Rafael Maldonado Lopez, Barcelona (ES)

(73) Assignee: Universitat Pompeu Fabra (ES)

( * ) Notice: Subject to any disclaimer, the term of this patent is extended or adjusted under 35 U.S.C. 154(b) by 0 days.

(21) Appl. No.: 14/778,266

(22) PCT Filed: Mar. 19, 2013

(86) PCT No.: PCT/EP2013/055728
§ 371 (c)(1),
(2) Date: Sep. 18, 2015

(87) PCT Pub. No.: WO2014/146699
PCT Pub. Date: Sep. 25, 2014

(65) Prior Publication Data
US 2016/0067235 A1  Mar. 10, 2016

(51) Int. Cl.
*A61K 31/50* (2006.01)
*A61K 31/445* (2006.01)
*A61K 31/44* (2006.01)
*A61K 31/35* (2006.01)
*A61K 31/454* (2006.01)
*A61K 31/337* (2006.01)
*A61K 31/353* (2006.01)
*A61K 31/415* (2006.01)
*A61K 31/52* (2006.01)
*A61K 31/352* (2006.01)
*A61K 31/397* (2006.01)

(52) U.S. Cl.
CPC .......... *A61K 31/454* (2013.01); *A61K 31/337* (2013.01); *A61K 31/352* (2013.01); *A61K 31/353* (2013.01); *A61K 31/397* (2013.01); *A61K 31/415* (2013.01); *A61K 31/44* (2013.01); *A61K 31/52* (2013.01)

(58) Field of Classification Search
CPC .. C07D 487/04; C07D 213/65; A61K 31/445; A61K 31/35
USPC ................ 514/249, 317, 351, 455
See application file for complete search history.

(56) References Cited

U.S. PATENT DOCUMENTS

2006/0276549 A1*  12/2006  Jacobson ............ A61K 31/454
514/649

2008/0004313 A1*  1/2008  Huang ................. C07D 231/14
514/326
2008/0255093 A1*  10/2008  Tam ...................... A61K 31/133
514/217.01
2009/0264436 A1*  10/2009  McKelvey ........... A61K 9/1635
514/249

FOREIGN PATENT DOCUMENTS

| WO | 2004/078261 A1 | 9/2004 |
| WO | 2005/091987 A2 | 10/2005 |
| WO | 2005/120496 A2 | 12/2005 |
| WO | 2007/088034 A2 | 8/2007 |
| WO | 2010/020585 A1 | 2/2010 |
| WO | 2011/109398 A2 | 9/2011 |

OTHER PUBLICATIONS

Arnau Busquets-Garcia et al: "Targeting the endocannabinoid system in the treatment of fragile X syndrome", Nature Medicine, Mar. 31, 2013 (Mar. 31, 2013), XP055061243, ISSN: 1078-8956, DOI: 10.1038/nm.3127.
Baudry M et al. Neurobiol Dis vol. 47, No. 2, 2012, pp. 210-5.
Chapleau Ca et al. Neurobiol Dis vol. 35, No. 2, 2009, pp. 219-33.
Dan B Epilepsia vol. 50, No. 11, 2009, pp. 2331-9.
B. M. Dolan et al: "Rescue of fragile X syndrome phenotypes in Fmr1 KO mice by the smallmolecule PAK inhibitor FRAX486", Proceedings of the National Academy of Sciences, vol. 110, No. 14, Mar. 18, 2013, (Mar. 18, 2013), pp. 5671-5676, XP055061530, ISSN: 0027-8424, DOI: 10.1073/pnas.1219383110.
Genebank database by the Gene ID: 1268 (Feb. 25, 2013).
Lee KW. et al. Proc Nail Acad Sci USA. vol. 103, No. 9, 2006, pp. 3399-404.
Machado-Salas JP Clin Neuropathol vol. 3, No. 2, 1984, pp. 52-8.
Martinez De Lagran, M. et al. Cereb Cortex vol. 22, No. 12, 2012, pp. 2867-77.
Remington's Pharmaceutical Sciences', 1990, Mack Publishing Company p. 1445.
Ken Soderstrom et al: "Altered patterns of filopodia production in CHO cells heterologously expressing zebra finch CB1 cannabinoid receptors", Cell Adhesion & Migration, vol. 6, No. 2, Mar. 1, 2012 (Mar. 1, 2012), pp. 91-99, XP055061529, ISSN: 1933-6918, DOI: 10.4161/cam.20164.
Tavazoie SF Nat Neurosci vol. 8, No. 12, 2005, pp. 1727-34.
Ward, Sara Jane et al: "Rimonabant Redux and Strategies to Improve the Future Outlook of CB1 Receptor Neutral-Antagonist/Inverse-Agonist Therapies", Obesity, 19(7), 1325-1334 Coden: Obesax; ISSN: 1930-7381, 2011, XP002696357.
Wiley et al. JPET vol. 340, 2012, pp. 433-44.

\* cited by examiner

*Primary Examiner* — Raymond Henley, III
(74) *Attorney, Agent, or Firm* — Banner & Witcoff, Ltd.

(57) ABSTRACT

The invention relates to antagonists of the cannabinoid receptor CBI for use in the treatment and prevention of diseases associated with neural dendritic abnormalities, such as Down's syndrome, Angelman's syndrome, Rett syndrome and tuberous sclerosis. More specifically, the invention provides a method of treatment or prevention of such diseases by the administration of the compound rimonabant.

17 Claims, 1 Drawing Sheet

A
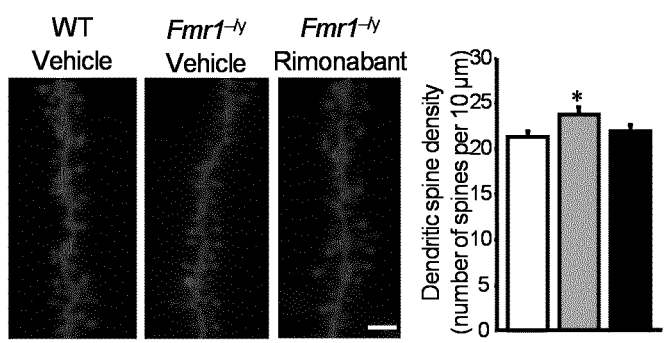
B
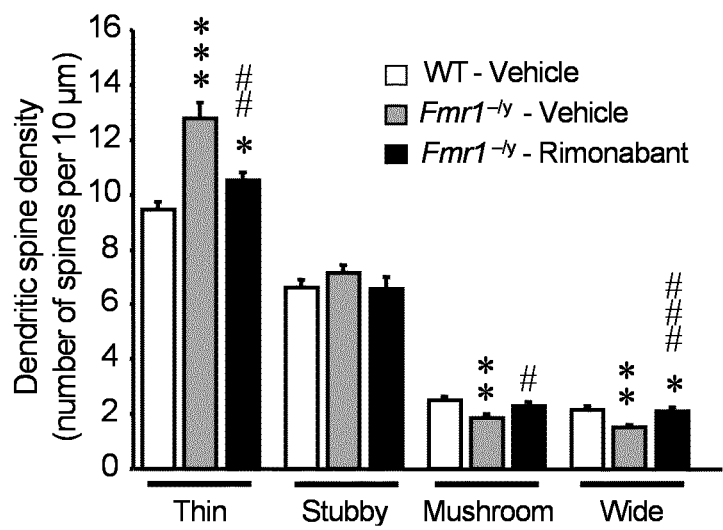

ANTAGONISTS OF THE CANNABINOID RECEPTOR CB1 FOR USE IN THE TREATMENT OF DISEASES ASSOCIATED WITH NEURONAL DENDRITIC ABNORMALITIES

RELATED APPLICATION DATA

This application is a National Stage Application under 35 U.S.C. 371 of co-pending PCT application number PCT/EP2013/055728 designating the United States and filed Mar. 19, 2013 and is hereby incorporated herein by reference in its entirety for all purposes.

FIELD OF THE INVENTION

The present invention relates to antagonists of the cannabinoid receptor CB1 for use in the prevention and/or treatment of diseases associated with neuronal dendritic abnormalities.

BACKGROUND OF THE INVENTION

The dendritic architecture determines the inputs in a neuron and its role in the neuronal circuitry. Dendritic arbors are highly dynamic structures, branching and retracting in response to the information received, and stabilized and maintained mainly by postsynaptic signaling.

The so-called dendritic pathologies are a number of diseases that share a feature of neuronal dendritic abnormalities (reviewed in Kaufmann and Moser, 2000). These include changes in dendrite branching patterns, fragmentation of dendrites, retraction or loss of dendrite branching, and changes in spine morphology and number. Dendritic spines are small membranous protrusions from a dendrite with spine head volumes ranging 0.01 $\mu m^3$ to 0.8 $\mu m^3$. Spines with strong synaptic contacts typically have a large spine head, which connect to the dendrite via a membranous neck. The most notable classes of spine shapes are "thin", "stubby", "mushroom" and "wide": thin spines have a smaller head and a narrow neck; stubby spines have no obvious constriction between the head and the attachment to the shaft; mushroom spines have a large head and a narrow neck; and wide spines are short in length and characterized by a large neck and a large spine head. Electron microscopy studies have shown that there is a continuum of shapes between these categories. The variable spine shape and volume is thought to be correlated with the strength and maturity of each spine-synapse: the thin and stubby types are considered to be immature forms whereas the mushroom and wide types are considered to be mature forms of spines.

Dendritic abnormalities and specially alterations in dendritic spines have been reported to contribute to several conditions associated with mental retardation, such as Down syndrome (Martinez de Langran, 2012), Angelman syndrome (Dan, 2009; Baudry et al., 2012) and Rett syndrome and to other neurological diseases, such as tuberous sclerosis (Machado-Salas, 1984; Tavazoie et al., 2005 (Chapeau et al., 2009).

The treatment of these dendritic pathologies has been addressed through different approaches without success so far. Treatment of genetic diseases causing mental retardation is mainly focussed on controlling symptoms and any medical conditions derived from said diseases. However, in the last years important efforts have been made to develop therapies targeted to those genes or proteins that have been found to be altered in these conditions. Thus, for example, some studies have shown that restoring MECP2 function, especially by the use of insulin-like growth factor 1 (IGF-1) may be a promising therapy for Rett syndrome. The molecule RG1662, which is an inverse agonist of the GABA-A receptor, a major inhibitory gateway in neuron circuitry, is now under phase I clinical trial in individuals with Down syndrome. Similarly, the mTOR inhibitor rapamycin, which has been found to improve brain function and reduce tumor size in a mouse model of tuberous sclerosis, in under clinical trials.

However, none of these novel therapies has at present proved to fully manage the disease. Therefore, there is still a need in the art for new methods of treatment for diseases associated with neuronal dendritic abnormalities.

BRIEF DESCRIPTION OF THE FIGURES

FIG. 1. (A) Representative staining with DiOlistics of hippocampal dendrites in the CA1 field of the hippocampus (left panel) and overall dendritic spine counts after pharmacological treatments (middle panel). Scale bar: 2 µm. Data are expressed as mean±s.e.m. *P<0.05 (Fmr1$^{-/y}$ versus WT). (B) Morphological analysis of dendritic spines in the CA1 field of the hippocampus after pharmacological treatments. Data are expressed as mean±s.e.m. *P<0.05, P<0.01, *P<0.001 (Fmr1$^{-/y}$ versus WT); #P<0.05, ###P<0.001 (rimonabant versus vehicle).

SUMMARY OF THE INVENTION

The inventors of the present invention have observed that, surprisingly, the administration of an antagonist of the cannabinoid receptor CB1 (such as a neutral antagonist or an inverse-agonist of the cannabinoid receptor CB1) and more specifically the administration of rimonabant is able to revert the altered spine density and morphology of the CA1 pyramidal neurons of Fmr1 knockout mice. Therefore, the administration of an antagonist, more specifically a neutral antagonist or an inverse-agonist, of the cannabinoid receptor CB1, such as rimonabant, is useful for the treatment of those pathologies that are associated with neuronal dendritic alterations.

Thus, in one aspect, the present invention refers to antagonists, more specifically neutral antagonists or inverse-agonists, of the cannabinoid receptor CB1 for use in the prevention or treatment of a disease associated with neuronal dendritic abnormalities.

In another aspect, the invention refers to the use of antagonists, more specifically neutral antagonists or inverse-agonists, of the cannabinoid receptor CB1 for the manufacture of a medicament for treating or preventing a disease associated with neuronal dendritic abnormalities.

In a further aspect, the invention refers to a method of treatment or prevention of a disease associated with neuronal dendritic abnormalities in a subject, comprising administering to said subject a therapeutically effective amount of an antagonist, more specifically a neutral antagonist or an inverse-agonist, of the cannabinoid receptor CB1.

DETAILED DESCRIPTION OF THE INVENTION

In one aspect, the present invention refers to an antagonist, more specifically a neutral antagonist or an inverse-agonist, of the cannabinoid receptor CB1 for use in the prevention or treatment of a disease associated with neuronal dendritic abnormalities.

In another aspect, the invention refers to the use of an antagonist, more specifically a neutral antagonist or an inverse-agonist, of the cannabinoid receptor CB1, for the manufacture of a medicament for treating or preventing a disease associated with neuronal dendritic abnormalities.

In a further aspect, the invention refers to a method of treatment or prevention of a disease associated with neuronal dendritic abnormalities in a subject, comprising administering to said subject a therapeutically effective amount of an antagonist, more specifically a neutral antagonist or an inverse-agonist, of the cannabinoid receptor CB1.

The term "cannabinoid receptor CB1" or "CB1R", as used herein, refers to a member of the family of the cannabinoid receptors, which are G protein-coupled receptors that are activated by cannabinoids. The cannabinoid receptor CB1 is mainly expressed in the central nervous system, but also in the lungs, liver and kidney. In humans the cannabinoid receptor CB1 is encoded by the gene CNR1, identified in the Genebank database by the Gene ID: 1268 (Feb. 25, 2013).

The term "antagonist of the cannabinoid receptor CB1", as used herein, refers to any molecule that binds to the cannabinoid receptor CB1 and lacks any substantial ability to activate the receptor itself. An antagonist can thereby prevent or reduce the functional activation or occupation of the receptor by an agonist such as anandamide when the agonist is present. The term "antagonist of the cannabinoid receptor CB1", as used herein, is intended to encompass both cannabinoid receptor CB1 neutral antagonists and inverse agonists. A "neutral antagonist" is a compound that blocks the action of the agonist but has no effect on intrinsic or spontaneous receptor activity. An "inverse agonist" is able to both blocks the action of the agonist at the receptor and attenuates the constitutive activity of the receptor.

The person skilled in the art knows how to determine the affinity of a particular molecule for the cannabinoid receptor CB1 and thus, to determine if this particular molecule is an antagonist of the cannabinoid receptor CB1. For example, the cannabinoid receptor CB1 affinity of a molecule can be determine using the methodology described by Wiley et at (Wiley et al, JPET 2012, 340: 433-44). Briefly, membrane preparations of Chinese hamster ovary (CHO) cells in which the human cannabinoid receptor CB1 has been stably transfected are incubated with the radioligands [$^3$H]SR141716 (for CB1 cannabinoid receptor) or [$^3$H]CP55,940 (for both CB1 and CB2 cannabinoid receptors) in the absence or presence of various concentrations of the test compound. After termination of the binding assay by rapid filtration under vacuum through Whatman GF/B glass fiber filters and exhaustive washing, bound radioactivity is determined by liquid scintillation spectrophotometry. Further, the patent application WO2004078261A1 (pages 20 to 28) discloses assays that can be performed by the person skilled in the art to distinguish the cannabinoid receptor antagonists (both neutral antagonists and inverse agonists); briefly, cannabinoid receptor ligands may be functionally characterized, for example, according to:

(i) Their effect upon adenylyl cyclase activity; and/or
(ii) Their effect upon [$^{35}$S]-g-GTP binding.

An inverse agonist will (i) stimulate adenylyl cyclase activity and (ii) inhibit [$^{35}$S]-g-GTP binding. A neutral antagonist will (i) block the inhibition of adenylyl cyclase activity by a CB1 agonist and (2) block the stimulation of [$^{35}$S]-g-GTP binding by a CB1 agonist.

In some embodiments, the antagonist of the cannabinoid receptor CB1 has an IC$_{50}$ from about 1 μM to about 1 nM. In other embodiments, the antagonist has an IC$_{50}$ from about 0.1 μM to 0.01 μM, 1.0 μM to 0.1 μM, or 0.01 μM to 1 nM. Preferably, such a cannabinoid antagonist is selective for the CB1 receptor and has an IC$_{50}$ for the CB1 receptor which is one-fourth or less than that of the CB2 receptor or, more preferably, is one-tenth or less than the IC$_{50}$ for the CB2 receptor, or even more preferably, an IC$_{50}$ with respect to the CB1 receptor which is one-hundredth that for the CB2 receptor.

The antagonists of the cannabinoid receptor CB1 can be, among others, proteins, peptides or small organic molecules. Illustrative non-limitative examples of antagonists of the cannabinoid receptor CB1 include the compounds of Table 1 or pharmaceutically acceptable salts thereof.

In a particular embodiment, the antagonist of the cannabinoid receptor CB1 is selected from the group consisting of the compounds of Table 1 or pharmaceutically acceptable salts thereof

TABLE 1

| Name | Formula |
|---|---|
| SR141716A (Rimonabant) 5-(4-Chlorophenyl)-1-(2,4-dichlorophenyl)-4-methyl-N-(piperidin-1-yl)-1H-pyrazole-3-carboxamide | |
| AM4113 | |

TABLE 1-continued

| Name | Formula |
|---|---|
| AM251<br>1-(2,4-dichlorophenyl)-5-(4-iodophenyl)-<br>4-methyl-N-(1-piperidyl)pyrazole-3-<br>carboxamide | |
| VCHSR1<br>5-(4-chlorophenyl)-3-[(E)-2-<br>cyclohexylethenyl]-1-(2,4-<br>dichlorophenyl)-4-methyl-1H-pyrazole | |
| AM6527 | |
| BPR0432 | |

TABLE 1-continued

| Name | Formula |
|---|---|
| O-2050 (6aR,10aR)-3-(1-methanesulfonylamino-4-hexyn-6-yl)-6a,7,10,10a-tetrahydro-6,6,9-trimethyl-6H-dibenzo[b,d]pyran | |
| MK0364 (Taranabant) N-[(2S,3S)-4-(4-chlorophenyl)-3-(3-cyanophenyl)-2-butanyl]-2-methyl-2-{[5-(trifluoromethyl)-2-pyridinyl]oxy}propanamide | |
| SR147778 (Surinabant) 5-(4-bromophenyl)-1-(2,4-dichlorophenyl)-4-ethyl-N-(1-piperidinyl)-1H-pyrazole-3-carboxamide | |
| SLV319 or BMS.646,256 (Ibipinabant) 4S-(−)-3-(4-chlorophenyl)-N-methyl-N'-[(4-chlorophenyl)-sulfonyl]-4-phenyl-4,5-dihydro-1H-pyrazole-1-carboxamidine | |
| AVE1625 (Drinabant) (±)-N-{1-[bis(4-chlorophenyl)methyl]-3-azetidinyl}-N-(3,5-difluorophenyl)methanesulfonamide | |

TABLE 1-continued

| Name | Formula |
|---|---|
| CP-945,598 (Otenabant)<br>1-[8-(2-chlorophenyl)-9-(4-chlorophenyl)-9H-purin-6-yl]-4-(ethylamino)piperidine-4-carboxamide | 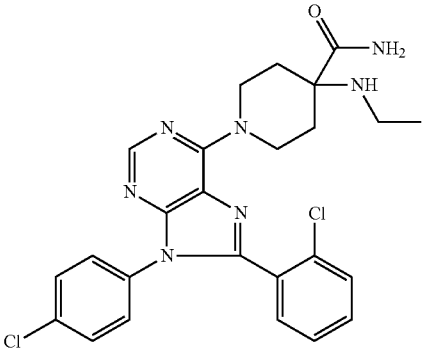 [SMILES: CCNC1(C(N)=O)CCN(c2ncnc3c2nc(-c2ccccc2Cl)n3-c2ccc(Cl)cc2)CC1] |
| E-6776 (Rosonabant)<br>(±)-5-(4-chlorophenyl)-1-(2,4-dichlorophenyl)-N-(1-piperidinyl)-4,5-dihydro-1H-pyrazole-3-carboxamide | 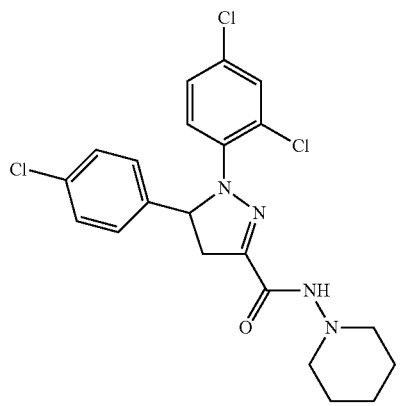 [SMILES: O=C(NN1CCCCC1)C1=NN(c2ccc(Cl)cc2Cl)C(c2ccc(Cl)cc2)C1] |
| TM38837<br>1-(2,4-dichlorophenyl)-4-ethyl-5-(5-(2-(4-(trifluoromethyl)phenyl)ethynyl)thiophen-2-yl)-N-(piperidin-1-yl)-1H-pyrazole-3-carboxamide | 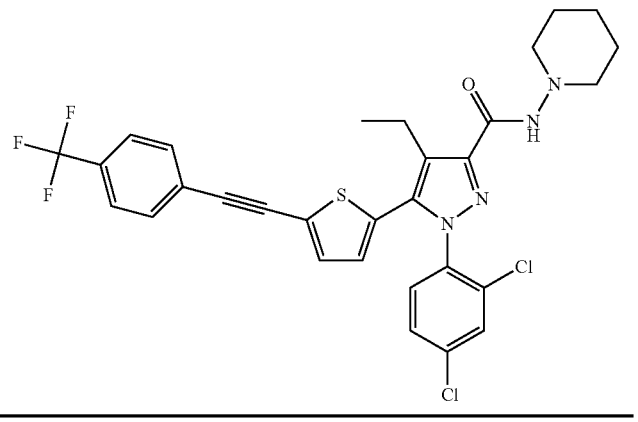 |

The term "pharmaceutically acceptable salt thereof", as used herein, refers to derivatives of the compounds of Table 1 wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the compounds of Table 1 can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two;

generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445.

In a preferred embodiment of the invention, the antagonist of the cannabinoid receptor CB1 is the compound 5-(4-Chlorophenyl)-1-(2,4-dichloro-phenyl)-4-methyl-N-(piperidin-1-yl)-1H-pyrazole-3-carboxamide (or "rimonabant" or "SR141716A") or a pharmaceutically acceptable salt thereof. Thus, in a particular embodiment, the invention is related with the compound 5-(4-Chlorophenyl)-1-(2,4-dichloro-phenyl)-4-methyl-N-(piperidin-1-yl)-1H-pyrazole-3-carboxamide or a pharmaceutically acceptable salt thereof for use in the prevention or treatment of a disease associated with neuronal dendritic abnormalities.

The term "prevention", as used herein, means that the antagonist of the cannabinoid receptor CB1, preferably the compound 5-(4-Chlorophenyl)-1-(2,4-dichloro-phenyl)-4-methyl-N-(piperidin-1-yl)-1H-pyrazole-3-carboxamide or a pharmaceutically acceptable salt thereof, is useful when administered to a patient who has not been diagnosed as possibly having the disorder or disease at the time of administration, but who would normally be expected to develop the disorder or disease or be at increased risk for the disorder or disease. According to the invention, the cannabinoid receptor CB1, preferably the compound 5-(4-Chlorophenyl)-1-(2,4-dichloro-phenyl)-4-methyl-N-(piperidin-1-yl)-1H-pyrazole-3-carboxamide or a pharmaceutically acceptable salt thereof, will slow the development of the disorder or disease symptoms, delay the onset of the disorder or disease, or prevent the individual from developing the disorder or disease at all.

The term "treatment", as used herein, refers to any process, action, application, therapy, or the like, wherein a subject (or patient), including a human being, is provided medical aid with the object of improving the subject's condition, directly or indirectly, or slowing the progression of a condition or disorder in the subject, or ameliorating at least one symptom of the disease or disorder under treatment.

The term "patient" or "subject", as used herein, refers to any animal, preferably a mammal and includes, but is not limited to, domestic and farm animals, primates and humans, for example, human beings, non-human primates, cows, horses, pigs, sheep, goats, dogs, cats, or rodents. In a preferred embodiment, the subject is a human being of any age or race. In a particular embodiment, the subject suffers from a disease associated with neuronal dendritic abnormalities. In another particular embodiment, the subject has not been diagnosed as suffering from a disease associated with neuronal dendritic abnormalities but is considered to be at increased risk of developing said disease.

The term "disease associated with neuronal dendritic abnormalities", as used herein, refers to a condition presenting with neuronal dendritic abnormalities. Preferably, said dendritic abnormalities are not caused by an external stimulus, but due to an impaired maturation of the neuronal dendritic plasticity. The dendritic abnormalities can affect the pyramidal neurons. The term "pyramidal neuron" or "pyramidal cell", as used herein, refers the a type of neurons present in the cerebral cortex, the hippocampus and the amygdala and characterized by a triangular shaped soma, a single axon, a large apical dendrite together with multiple basal dendrites and dendritic spines. The pyramidal neurons are involved in cognitive ability, playing a critical role in complex object recognition within the visual processing areas of the cortex. Thus, in a particular embodiment, the disease associated with neuronal dendritic abnormalities is a disease associated with pyramidal neuronal dendritic abnormalities. The term "dendritic abnormalities", as used herein, refers to a change in the number and length of dendritic branches or to an aberrant morphology and number of dendritic spines. The term "spine" or "dendritic spine", as used herewith, refers to a small membranous protrusion from a neuron dendrite that typically receives input from a single synapse of an axon. In a particular embodiment, the neuronal dendritic abnormalities are an increased spine number and/or density. In another particular embodiment, the neuronal dendritic abnormalities are an aberrant morphology of the dendritic spines. In another particular embodiment, the dendritic abnormalities are increased spine number and/or density and aberrant morphology of the dendritic spines.

In a more particular embodiment, the neuronal dendritic abnormalities are increased number of immature spines (thin and stubby spines). The classification criteria of dendritic spine morphology commonly used in the art is based in head diameter, neck diameter, overall length and other geometric dimensions to describe the spines both qualitatively and quantitatively. Briefly, protrusions from dendrites are classified into five types based on their morphology: class 1 protrusions, also called stubby protuberances are 0.5 mm in length, lacked a large spine head, and do not appear to have a neck; class 2, or mushroom-shaped spines are between 0.5 and 1.25 mm in length and are characterized by a short neck and large spine head; class 3, or thin spines range between 1.25 and 3.0 mm and have elongated spine necks with small heads; class 4 or wide spines are between 0.5 and 1.25 mm in length and are characterized by a large neck and a large spine head; and class 5 or branched spines range between 1.25 and 3.0 mm and have elongated spine necks with two or more spine heads.

Illustrative non-limitative examples of diseases associated with neuronal dendritic abnormalities are Down syndrome, Angelman syndrome, Rett syndrome and tuberous sclerosis.

In a particular embodiment, the disease associated with neuronal dendritic abnormalities is selected from the group consisting of Down syndrome, Angelman syndrome, Rett syndrome and tuberous sclerosis.

The term "Down syndrome" or "trisomy 21", as used herein, refers to a chromosomal condition caused by the presence of all or part of a third copy of chromosome 21. It is typically associated with a delay in cognitive ability and physical growth, and a particular set of facial characteristics. Cognitive dysfunction in Down's syndrome patients is correlated with reduced dendritic branching and complexity, along with fewer spines of abnormal shape in the cortical neurons (Martinez de Lagran, M. et al, Cereb Cortex 2012, 22(12): 2867-77).

The term "Angelman syndrome", as used herein, refers to a complex neuro-genetic disorder characterized by delayed development, intellectual disability, severe speech impairment, motor impairment and epilepsy. Angelman syndrome is caused by deficient UBE3A gene expression that may be caused by various abnormalities on the maternally inherited chromosome 15. Recent findings in animal models demonstrated altered dendritic spine formation in various brain regions, including hippocampus and cerebellar cortex (Dan B, Epilepsia 2009, 50(11): 2331-9) and defective activity-driven spine cytoskeletal reorganization (Baudry M et al, Neurobiol Dis 2012, 47(2): 210-5).

The term "Rett syndrome", as used herein, refers to an X chromosome-linked neurodevelopmental disorder that leads to developmental reversals, especially in the areas of expressive language and hand use. The clinical features include small hands and feet and a deceleration of the rate of head growth, including microcephaly in some cases. Rett syndrome is associated with neurophatologies of dendritic spines, in particular reduced dendritic spine density in hippocampal pyramidal neurons has been found in patients with Rett syndrome (Chapleau C A et al, Neurobiol Dis 2009, 35(2): 219-33).

The term "tuberous sclerosis" or "Bourneville's disease", as used herein, refers to a neurocutaneous syndrome caused by mutations in one of either of two genes, TSC1 and TSC2, which encode proteins hamartin and tuberin respectively, both of which act as tumor suppressors. Tuberous sclerosis leads to the growth of non-malignant tumors in the brain and other vital organs such as kidneys, heart, eyes, lungs and skin. Different types of dendritic abnormalities have been described in tuberous sclerosis patients (Machado-Salas J P, Clin Neuropathol 1984, 3(2): 52-8) and in mice lacking Tsc1 or Tsc2 expression (Tavazoie S F, Nat Neurosci 2005, 8(12): 1727-34).

In a particular embodiment of the invention Rimonabant is used in the treatment or prevention of a disease associated with neuronal dendritic abnormalities selected from the group consisting of Down syndrome, Angelman syndrome, Rett syndrome and tuberous sclerosis.

In a particular embodiment, the disease associated with neuronal dendritic abnormalities is Down syndrome.

In another particular embodiment, the disease associated with neuronal dendritic abnormalities is Angelman syndrome.

In another particular embodiment, the disease associated with neuronal dendritic abnormalities is Rett syndrome.

In another particular embodiment, the disease associated with neuronal dendritic abnormalities is tuberous sclerosis.

The method of administration of the antagonist of the cannabinoid receptor CB1, preferably the compound 5-(4-Chlorophenyl)-1-(2,4-dichloro-phenyl)-4-methyl-N-(piperidin-1-yl)-1H-pyrazole-3-carboxamide or a pharmaceutically acceptable salt thereof, will depend on the disease to be treated and other factors such as duration of the therapy and whether the antagonist of the cannabinoid receptor CB1, preferably the compound 5-(4-Chlorophenyl)-1-(2,4-dichloro-phenyl)-4-methyl-N-(piperidin-1-yl)-1H-pyrazole-3-carboxamide or a pharmaceutically acceptable salt thereof, will be administered for preventing or treating purposes. Thus, the antagonist of the cannabinoid receptor CB1, preferably the compound 5-(4-Chlorophenyl)-1-(2,4-dichloro-phenyl)-4-methyl-N-(piperidin-1-yl)-1H-pyrazole-3-carboxamide or a pharmaceutically acceptable salt thereof can be administered chronically, sub-chronically or acutely.

The term "chronically", as used herein, refers to a method of administration wherein the antagonist of the cannabinoid receptor CB1, preferably the compound 5-(4-Chlorophenyl)-1-(2,4-dichloro-phenyl)-4-methyl-N-(piperidin-1-yl)-1H-pyrazole-3-carboxamide or a pharmaceutically acceptable salt thereof, is administered continuously to the patient for extended periods of time in order to maintain the therapeutic effect during this period. Chronic administration forms include the daily administration of multiples doses of the compound, twice daily, three times daily or more frequently. Alternatively, chronic administration can involve the administration as a bolus or by continuous transfusion which can be performed daily, every two days, every 3 to 15 days, every 10 days or more. Typically, chronic administration is continued for at least one week, at least 7 weeks, at least 8 weeks, at least 9 weeks, at least 10 weeks, at least 11 weeks, at least 12 weeks, at least four months, at least 5 months, at least 6 months, at least 9 months, at least one year, at least two years or more.

The term "acutely", as used herein, refers to a method of administration in which the patient is exposed to a single dose of the antagonist of the cannabinoid receptor CB1, preferably the compound 5-(4-Chlorophenyl)-1-(2,4-dichloro-phenyl)-4-methyl-N-(piperidin-1-yl)-1H-pyrazole-3-carboxamide or a pharmaceutically acceptable salt thereof, or a multiple dose but for a reduced period of time like for example 1, 2, 4, 6, 8, 10, 12, 16, 20, 24 hours or 2, 3, 4, 5, or 6 days.

In a particular embodiment, the antagonist of the cannabinoid receptor CB1, preferably the compound -(4-Chlorophenyl)-1-(2,4-dichloro-phenyl)-4-methyl-N-(piperidin-1-yl)-1H-pyrazole-3-carboxamide or a pharmaceutically acceptable salt thereof is administered chronically, preferably for a period of at least 7 days.

The antagonist of the cannabinoid receptor CB1, preferably the compound -(4-Chlorophenyl)-1-(2,4-dichloro-phenyl)-4-methyl-N-(piperidin-1-yl)-1H-pyrazole-3-carboxamide or a pharmaceutically acceptable salt thereof, may be administered by any suitable administration route, such as, but not limited to, parenteral, oral, topical, nasal, rectal route. In a particular embodiment, the antagonist of the cannabinoid receptor CB1, preferably the compound -(4-Chlorophenyl)-1-(2,4-dichloro-phenyl)-4-methyl-N-(piperidin-1-yl)-1H-pyrazole-3-carboxamide or a pharmaceutically acceptable salt thereof, is administered orally. In another particular embodiment, the antagonist of the cannabinoid receptor CB1, preferably the compound -(4-Chlorophenyl)-1-(2,4-dichloro-phenyl)-4-methyl-N-(piperidin-1-yl)-1H-pyrazole-3-carboxamide or a pharmaceutically acceptable salt thereof is administered by parenteral route, e.g. by intravenous, intraperitoneal, intracranial, subcutaneous, intradermal, intramuscular, intrathecal or epidural administration. In a more particular embodiment, it is administered intraperitoneally. In another particular embodiment, it is administered intracraneally.

The term "therapeutically effective amount", as used herein, refers to the sufficient amount of the compound to provide the desired effect and will generally be determined by, among other causes, the characteristics of the compound itself and the therapeutic effect to be achieved. It will also depend on the subject to be treated, the severity of the disease suffered by said subject, the chosen dosage form, administration route, etc. For this reason, the doses mentioned in this invention must be considered only as guides for the person skilled in the art, who must adjust the doses depending on the aforementioned variables. In an embodiment, the effective amount produces the amelioration of one or more symptoms of the disease that is being treated.

In a particular embodiment, the cannabinoid receptor CB1, preferably the compound -(4-Chlorophenyl)-1-(2,4-dichloro-phenyl)-4-methyl-N-(piperidin-1-yl)-1H-pyrazole-3-carboxamide or a pharmaceutically acceptable salt thereof is administered intraperitoneally at 1 mg/kg of body mass per day, for seven consecutive days.

In another particular embodiment, the cannabinoid receptor CB1, preferably the compound -(4-Chlorophenyl)-1-(2,4-dichloro-phenyl)-4-methyl-N-(piperidin-1-yl)-1H-pyrazole-3-carboxamide or a pharmaceutically acceptable salt thereof is administered orally at 1 mg/kg of body mass per day, for seven consecutive days.

EXAMPLE

Dendritic Spine Density and Morphology Analysis in Fmr1$^{-/y}$ Mice Treated with Rimonabant Materials and Methods
Animals:

Fmr1 knockout (KO) mice in FVB background (Fmr1 KO, FVB.129P2-Pde6b$^+$ Tyr$^{c-ch}$ Fmr1$^{tm1Cgr}$/J) and wild-type mice (WT, FVB.129P2-Pde6b$^+$ Tyr$^{c-ch}$/AntJ) were purchased from The Jackson Laboratory and crossed to obtain Fmr1$^{-/y}$ and WT littermates. All experimental animals were bred in-house at the Barcelona Biomedical Research Park (PRBB) Animal Facility. Fmr1$^{-/y}$ and WT mice were used at 12 to 16 weeks of age. Mice were housed four per cage in a temperature (21±1° C.) and humidity (55±10%) controlled environment. Food and water were available ad libitum. All the experiments were performed during the light phase of a 12 h light/dark cycle (lights on at 8 am and off at 8 pm). Animals were handled for one week before starting the experiments. All animal procedures followed the standard ethical guidelines (European Communities Directive 86/60-EEC) and were approved by the local ethical committee (Comitè Èlic d'Experimentació Animal-Parc de Recerca Biomèdica de Barcelona, CEEA-PRBB). The PRBB has also the Animal Welfare Assurance (#A5388-01, IACUC Approval Date Jun. 8, 2009) granted by the Office of Laboratory Animal Welfare (OLAW) of the National Institutes of Health (USA). All behavioral tests were performed by researchers blind to the different experimental groups.
Drugs and Treatments:

Rimonabant was obtained from Sanofi-Aventis (Sanofi-Aventis Recherche). Rimonabant was injected intraperitoneally (i.p.) in a volume of 10 ml per kg.
Dendritic Spine Morphology Analysis:

Dendritic spine analysis was performed as previously described (Lee K W. et al., Proc Natl Acad Sci USA. 2006; 103(9): 3399-404) in mice that received a chronic administration of rimonabant (1 mg kg$^{-1}$, 7 d) or its vehicle. Brains were extracted after perfusion (4% PFA in PB) 3 h after the last administration of rimonabant or vehicle solution on the seventh day of treatment. Secondary to tertiary dendrites of pyramidal neurons from the CA1 region of the hippocampus were chosen for spine analysis based on the criteria described previously (Lee K W. et al., Proc Natl Acad Sci USA. 2006; 103(9): 3399-404).
Statistical Analysis:

Results are reported as mean±s.e.m. The experiments were evaluated by one-way analysis of variance (ANOVA) followed by the Dunnett's post-hoc test when required. Comparisons were considered statistically significant when P<0.05.
Results It has previously been reported that Fmr1$^{-/y}$ mice show a pattern of altered spine morphology in the dendrites of the CA1 field of the hippocampus when compared to wild type mice. Fmr1 KO mice were used as a model to evaluate the capacity of CB1 cannabinoid receptor antagonists to restore the abnormal spine morphology.

The enhanced dendritic spine density of CA1 pyramidal neurons in Fmr1$^{-/y}$ mice, an animal model of these type of diseases, was normalized by pharmacological blockade of the CB1 cannabinoid receptor antagonist rimonabant (1 mg/kg, i.p., 7 d) (FIG. 1). When spines were classified based on their morphology (right panel), rimonabant-treated Fmr1$^{-/y}$ mice showed a decrease in thin/stubby (immature) spines and an increase in mushroom/wide (mature) spines compared to vehicle-treated Fmr1$^{-/y}$ mice.

The invention claimed is:

1. A method of treatment of a disease associated with neuronal dendritic abnormalities in a subject in need thereof or of delaying the onset or slowing the development of symptoms of a disease associated with neuronal dendritic abnormalities in a subject at increased risk of developing a disease associated with neuronal dendritic abnormalities, comprising administering to said subject a therapeutically effective amount of an antagonist of the cannabinoid receptor CB1 selected from a neutral antagonist or an inverse-agonist of the cannabinoid receptor CB1.

2. The method according to claim 1, wherein said antagonist is selected from the group consisting of the compounds of Table 1 or pharmaceutically acceptable salts thereof.

3. The method according to claim 2, wherein said antagonist is the compound 5-(4-Chlorophenyl)-1-(2,4-dichlorophenyl)-4-methyl-N-(piperidin-1-yl)-1H-pyrazole-3-carboxamide or a pharmaceutically acceptable salt thereof.

4. The method according to claim 2, wherein said antagonist is selected from the group consisting of:
  1-(2,4-dichlorophenyl)-5-(4-iodophenyl)-4-methyl-N-(1-piperidyl)pyrazole-3-carboxamide,
  (6aR,10aR)-3-(1-methanesulfonylamino-4-hexyn-6-yl)-6a,7,10,10a-tetrahydro-6,6,9-trimethyl-6H-dibenzo[b,d]pyran,
  N-[(2S,3S)-4-(4-chlorophenyl)-3-(3-cyanophenyl)-2-butanyl]-2-methyl-2-{[5-(trifluoromethyl)-2-pyridinyl]oxy}propanamide,
  5-(4-bromophenyl)-1-(2,4-dichlorophenyl)-4-ethyl-N-(1-piperidinyl)-1H-pyrazole-3-carboxamide,
  4S-(−)-3-(4-chlorophenyl)-N-methyl-N'-[(4-chlorophenyl)-sulfonyl]-4-phenyl-4,5-dihydro-1H-pyrazole-1-carboxamidine,
  (±)-N-{1-[bis(4-chlorophenyl)methyl]-3-azetidinyl}-N-(3,5-difluorophenyl)-methanesulfonamide,
  1-[8-(2-chlorophenyl)-9-(4-chlorophenyl)-9H-purin-6-yl]-4-(ethylamino)piperidine-4-carboxamide,
and
  (±)-5-(4-chlorophenyl)-1-(2,4-dichlorophenyl)-N-(1-piperidinyl)-4,5-dihydro-1H-pyrazole-3-carboxamide
or a pharmaceutically acceptable salt thereof.

5. The method according to claim 2, wherein said antagonist is selected from the group consisting of:

Compound AM4113 of formula:

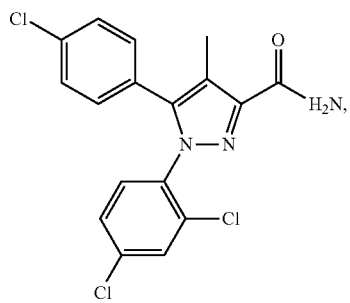 [SMILES: Cc1c(C(N)=O)nn(-c2ccc(Cl)cc2Cl)c1-c1ccc(Cl)cc1]

Compound VCHSR1 of formula:

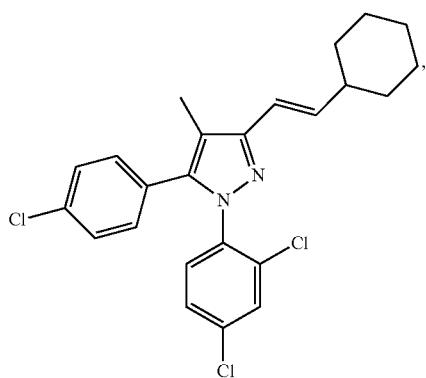 [SMILES: Cc1c(/C=C/C2CCCCC2)nn(-c2ccc(Cl)cc2Cl)c1-c1ccc(Cl)cc1]

Compound AM6527 of formula:

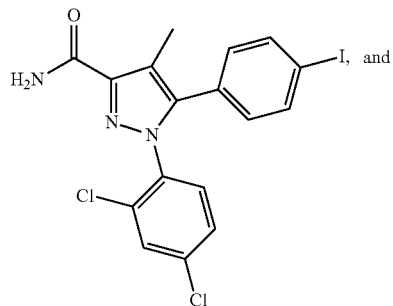 [SMILES: Cc1c(C(N)=O)nn(-c2ccc(Cl)cc2Cl)c1-c1ccc(I)cc1 ; "and"]

Compound BPR0432 of formula:

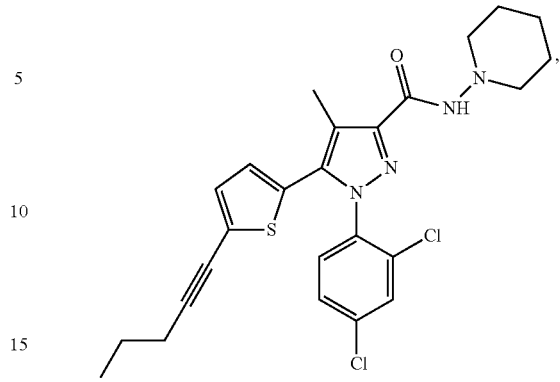

or a pharmaceutically acceptable salt thereof.

6. The method according to claim 1, wherein the disease is associated with pyramidal neuronal dendritic abnormalities.

7. The method according to claim 1, wherein the neuronal dendritic abnormalities are aberrant morphology and/or number of dendritic spines.

8. The method according to claim 7, wherein the number of dendritic spines is increased.

9. The method according to claim 8, wherein the number of immature spines (thin and stubby spines) is increased.

10. The method according to claim 1, wherein said antagonist is administered orally.

11. The method according to claim 1, wherein said antagonist is administered intraperitoneally.

12. The method according to claim 1, wherein said disease is selected from the group consisting of Down's syndrome, Angelman's syndrome, Rett syndrome and tuberous sclerosis.

13. The method according to claim 1, wherein said disease is caused by mutation invalidating the FMR1 gene.

14. The method according to claim 1, wherein said disease is Fragile X syndrome.

15. The method according to claim 4, wherein said disease is selected from the group consisting of Down's syndrome, Angelman's syndrome, Rett syndrome and tuberous sclerosis.

16. The method according to claim 4, wherein said disease is caused by mutation invalidating the FMR1 gene.

17. The method according to claim 4, wherein said disease is Fragile X syndrome.

* * * * *